US00PP30093P2

(12) United States Plant Patent
Olesen et al.

(10) Patent No.: US PP30,093 P2
(45) Date of Patent: Jan. 15, 2019

(54) ***CLEMATIS* PLANT NAMED 'EVIPO089'**

(50) Latin Name: *Clematis viticella*
Varietal Denomination: Evipo089

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/731,961

(22) Filed: Sep. 5, 2017

(51) Int. Cl.
*A01H 5/02* (2018.01)

(52) U.S. Cl.
USPC ..... Plt./228

(58) Field of Classification Search
USPC ..... Plt./226, 228
See application file for complete search history.

*Primary Examiner* — Susan McCormick Ewoldt

(57) ABSTRACT

A new *Clematis* plant with a compact growth habit, profuse, dark violet purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *viticella*.

Variety denomination: 'Evipo089'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo089' originated as a single seedling from the stated cross.

The new *clematis* plant may be distinguished from its female seed parent and male pollen parent by the following characteristics. The female seed parent has Purple Group 77A tepals while the new variety has dark violet purple tepals. The male seed parent has flowers with a diameter of 200 mm, while the new variety has tepals which are about 150 mm in diameter.

The objective of the hybridization of this *clematis* plant was to create a new and distinct variety for nursery culture with unique qualities such as:

1. Uniform and abundant dark violet purple flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo089' was selected by Mogens N. Olesen and Raymond J. Evison in their *clematis* development program in the Channel Islands, United Kingdom in 2006. Asexual reproduction of 'Evipo089' by means of vegetative cuttings and traditional layering was first performed by Mogens N. Olesen and Raymond J. Evison in the nursery during the summer of 2006. This initial and subsequent asexual propagations have demonstrated that the characteristics of 'Evipo089' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo089'.

Specifically illustrated in FIG. 1 of the drawings are open flowers, tepals detached, and reproductive flower parts.

DETAILED DESCRIPTION OF THE VARIETY

Figure 1:
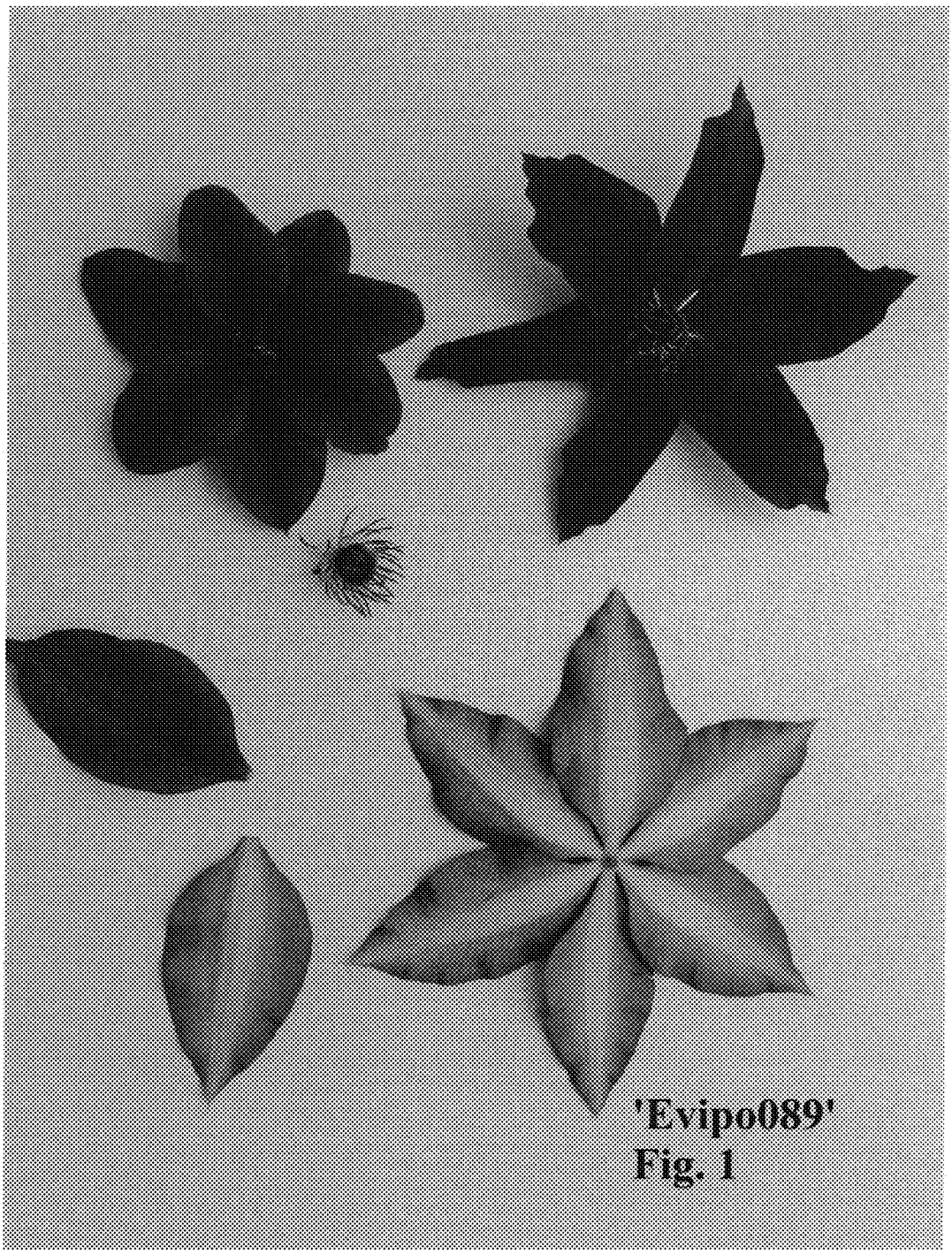
Figure 2:
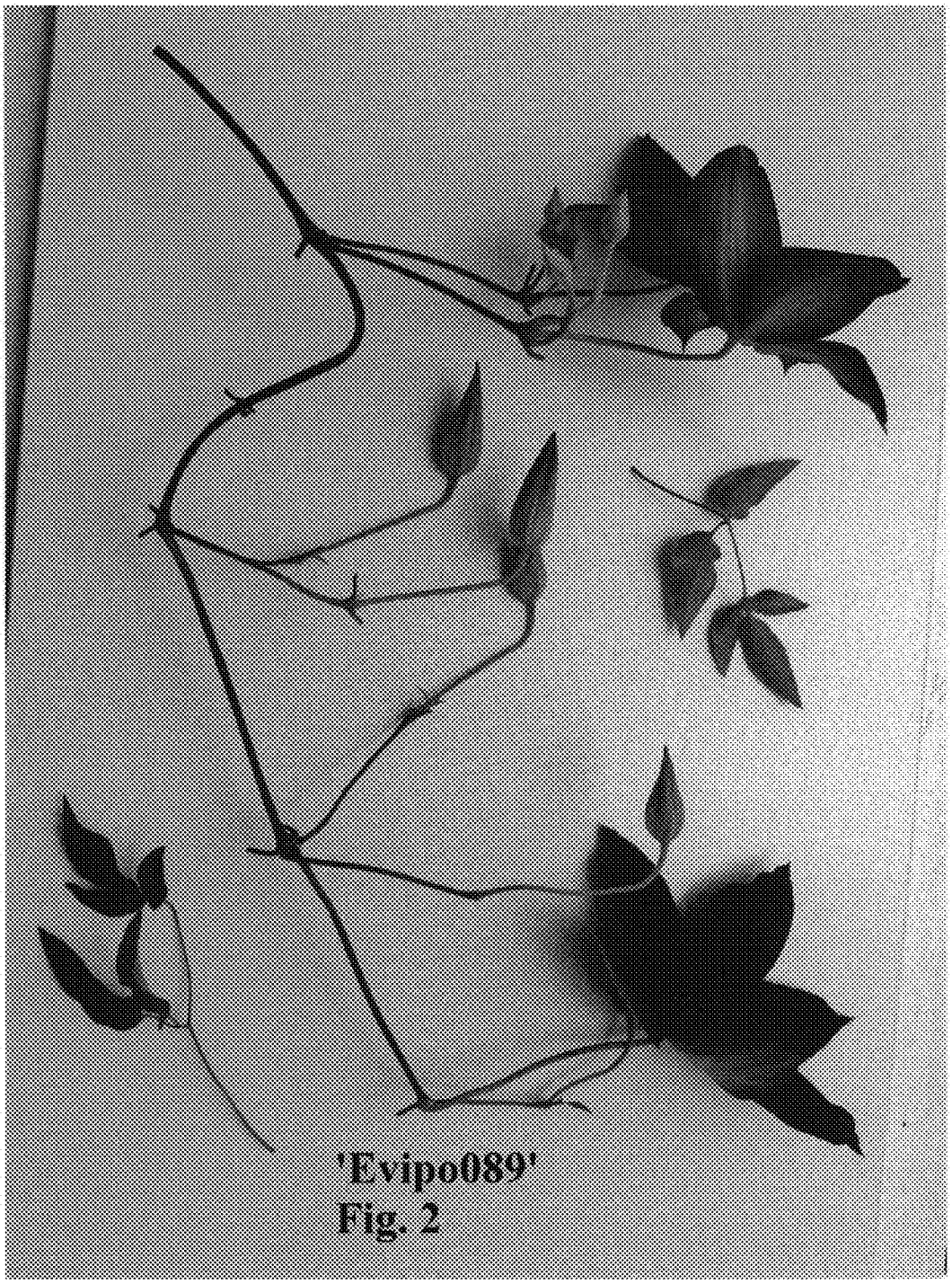
FIG. 2 shows a mature leaf with flowering branch exhibiting stems, and flower buds. Illustrated plants are 2 years of age.

The following is a detailed description of 'Evipo089', as observed in its growth throughout the flowering period in Marion County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo040' described and illustrated in U.S. Plant Pat. No. 25,608 are compared to 'Evipo089' in Chart 1.

CHART 1

| | 'Evipo089' | 'Evipo040' |
|---|---|---|
| Flower diameter | 160 | 150 mm |
| Tepal upper surface color upon opening | Violet Group 83A with intonations of Purple Group N79C | Violet Group 86B with light intonations of Purple Group 77B |
| Filament color on reproductive flower parts | Purple Group 76C | Yellow-Green Group 154C, Green White Group 157D |

Flower and Flower Bud

Blooming habit: Continuous. The natural flowering period is generally from April to September.

Flower bud:

*Size*.—Normally 30 mm in length. Bud diameter is 14 mm.

*Bud form*.—Long campanulate, broad based.

*Bud color*.—Yellow-Green Group 145A with intonations of Greyed-Orange Group 177B at the apex.

*Texture*.—Pubescent.

Pedicel:

*Surface texture*.—Smooth.

*Length*.—On average 60 mm in length with 2 mm diameter.

*Color*.—Yellow-Green Group 144A with intonations of Greyed-Purple Group 183B.

*Strength*.—Moderately strong.

Receptacle:

*Surface texture*.—Lightly pubescent.

*Shape*.—Broad funnel.

*Size*.—2 mm (h)×4 mm (w).

*Color*.—Yellow-Green Group 144A.

Flower arrangement:

*Location on vine*.—New and old growth.

*Borne*.—Normally in clusters of 12 to 15 flowers on each vine.

Flower bloom:

*Size*.—On average, flowers are 160 mm in diameter and 15 mm in depth.

*Profile*.—Open flowers are flat.

*Fragrance*.—None.

*Lasting quality*.—Flowers normally remain up to 10 days on the plant.

Tepals:

*Tepal color*.—Upon opening, the upper surface is Violet Group 83A with intonations of Purple Group N79C. The lower surface is Yellow-Green Group 145A at the central axis, afterward primarily Violet Group 83D at the margin with some intonations of Violet Group 85B and. After opening, the upper surface is colored with a central bar of Purple Group N78A and Violet Group 88A at margins. The lower surface is Yellow-Green Group 145C at the central axis, afterward primarily Violet Group 90B at the margin with some intonations of Violet Group N88A.

*Quantity*.—Normally 6 tepals.

*Size*.—80 mm in length by 42 mm wide.

*Shape*.—Individual tepal shape is elliptic. The tepal apex is acute. The tepal base is acute.

*Apex recurvature*.—None.

*Tepal cross section*.—Flat to slightly cupped.

*Margins*.—Entire. No undulations of margin observed.

*Persistence*.—Tepals fall off cleanly.

Reproductive organs:

*Pollen*.—None observed. Quantity: Scant. Color: White Group 155A.

*Anthers*.—Size: 8 mm in length. Color: Purple Group N79B. Quantity: On average, 55.

*Filaments*.—Color: Purple Group 76C. Length: 5 mm.

*Pistils*.—Quantity: On average, 35.

*Stigmas*.—Inferior in location relative to the length of the filaments and the height of the anthers.

*Styles*.—Color: Black Group 202A. At the stigma, Greyed Green Group 192D. Length: 6 mm.

Seed head characteristics: Seed not observed to date.

Plant

Plant form: Climbing.

Size: Seasons growth attains 100 cm in height. Average spread is 50 cm.

Stems:

*Color*.—Juvenile stems are Yellow-Green Group 144A. Mature stems are Greyed-Purple Group 184B.

*Internodes*.—On average, 11 cm between nodes.

*Length*.—Normally 10 cm from the base of the plant to the flowering portion of the stem.

*Diameter*.—About 3.5 mm.

*Texture*.—Mature stems are ribbed.

Plant foliage:

*Leaf characteristics*.—Deciduous.

*Arrangement*.—Trifoliate. Terminal leaflets are trilobed. Other leaflets are simple.

*Leaf size*.—Compound leaves are about 140 mm (l)×90 mm (w). Leaflets are about 65 mm (l)×30 mm (w).

*Abundance*.—On average 1 leaf per 10 cm of stem.

*Leaf color*.—Juvenile upper Yellow-Green Group 144A. Juvenile lower Yellow-Green Group 144A. Mature upper Yellow-Green Group 146C. Mature lower Yellow-Green Group 146B.

*Stipules*.—Absent.

*Petioles*.—Size: Normally 75 mm in length by 2 mm diameter. Texture: Smooth. Color: Greyed-Orange Group 177A.

*Petioloule*.—Size: About 20 mm in length by 1.5 mm diameter. Texture: Smooth. Color: Greyed-Orange Group 177A.

*Leaflet shape*.—Ovate, with terminal leaflets trilobed. The base is rounded, apex acute.

*Margin*.—Entire.

*Surface*.—The upper side is smooth, the lower side is smooth.

*Thickness*.—Moderate.

*Glossiness*.—Moderately glossy.

Disease resistance: Subject to any disease that normally attacks the species. However the variety is more tolerant to clematis wilt, Ascochyta clematidina, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo089', substantially as described and illustrated, due to its abundant dark violet purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo089'

'Evipo089'